United States Patent
Jin

(10) Patent No.: US 10,661,094 B2
(45) Date of Patent: May 26, 2020

(54) SYSTEMS AND METHODS FOR SPASTICITY TREATMENT USING SPINAL NERVE MAGNETIC STIMULATION

(71) Applicant: Kosivana Holdings Limited, Limassol (CY)

(72) Inventor: Yi Jin, Irvine, CA (US)

(73) Assignee: Wave Neuroscience, Inc., Newport Beach, CA (US)

(*) Notice: Subject to any disclaimer, the term of this patent is extended or adjusted under 35 U.S.C. 154(b) by 339 days.

(21) Appl. No.: 15/131,616

(22) Filed: Apr. 18, 2016

(65) Prior Publication Data
US 2017/0296837 A1 Oct. 19, 2017

(51) Int. Cl.
*A61N 2/00* (2006.01)
*A61N 2/02* (2006.01)

(52) U.S. Cl.
CPC .............. *A61N 2/004* (2013.01); *A61N 2/02* (2013.01)

(58) Field of Classification Search
CPC .................................. A61N 2/02; A61N 2/004
USPC ...................................................... 600/9–15
See application file for complete search history.

(56) References Cited

U.S. PATENT DOCUMENTS

| | | | | |
|---|---|---|---|---|
| 6,086,525 A | * | 7/2000 | Davey | A61N 2/006 600/13 |
| 6,443,883 B1 | * | 9/2002 | Ostrow | A61N 2/008 600/14 |
| 6,652,443 B1 | * | 11/2003 | Struppler | A61N 2/006 600/9 |
| 2002/0165583 A1 | * | 11/2002 | Tepper | A61N 2/02 607/2 |
| 2004/0176805 A1 | * | 9/2004 | Whelan | A61N 1/40 607/2 |
| 2005/0148808 A1 | * | 7/2005 | Cameron | A61G 15/125 600/13 |
| 2005/0228209 A1 | * | 10/2005 | Schneider | A61B 5/04009 600/13 |
| 2008/0262287 A1 | * | 10/2008 | Dussau | A61N 2/02 600/13 |
| 2014/0031605 A1 | * | 1/2014 | Schneider | A61N 2/006 600/14 |
| 2014/0058189 A1 | * | 2/2014 | Stubbeman | A61N 2/002 600/13 |
| 2014/0275718 A1 | * | 9/2014 | Huang | A61N 2/006 600/12 |
| 2015/0165226 A1 | * | 6/2015 | Simon | A61N 1/40 600/13 |

\* cited by examiner

*Primary Examiner* — Navin Natnithithadha
*Assistant Examiner* — Sunita Reddy
(74) *Attorney, Agent, or Firm* — Buchalter, a professional corp.; Kari L. Barnes

(57) ABSTRACT

Described are methods, devices, and systems for a novel, easy to use treatment for spasticity that does not involve medication. Methods and devices herein use low-frequency repetitive magnetic fields to enhance communication in the spinal nerve, thereby allowing improved relaxation, control, and coordination in a muscle.

11 Claims, 8 Drawing Sheets

SYSTEMS AND METHODS FOR SPASTICITY TREATMENT USING SPINAL NERVE MAGNETIC STIMULATION

BACKGROUND OF THE INVENTION

Muscle spasticity is a serious and sometimes debilitating condition. It is generally considered to result from a loss of inhibition of motor neurons, causing excessive muscle contraction or hyperreflexia. The altered skeletal muscle performance results in often severe contractions, twitching, and involuntary or jerky movements. In addition, those afflicted with the disorder may have joint stiffness, unusual posture, and exaggerated reflexes. Spasticity can cause pain, loss of sleep, joint deformity, macerated skin, loss of coordination, fatigue, and an inability to perform many basic daily activities.

Spastic cerebral palsy is by far the most common form of cerebral palsy (CP), occurring in more than 70% of all cases, affecting approximately 3 children out of every 1,000 people. Spasticity is also a symptom in 78% of multiple sclerosis patients, 35% of those with stroke, 50% of patients with traumatic brain injury (TBI), and 40% of those with spinal cord injury (SCI).

In general, spasticity develops when an imbalance occurs in the excitatory and inhibitory input to alpha motor neurons in the spinal cord, leading to hyper-excitability of the affected muscle or muscles. Possible mechanisms of action include lesions of the upper motor neuron, such as in CP, stroke, TBI, or SCI, where disruption occurs not only in the pyramidal tract, but also in the corticospinal tract involved in voluntary movement. Removal of inhibition on segmental polysynaptic pathways leads to a rise of the excitatory state due to cumulative excitation. In the cerebral model, enhanced excitability of monosynaptic pathways can cause a buildup of reflex activity.

Spasticity is often localized to a particular muscle or muscles in the body. Specific locations in the body communicate with the brain through at least one spinal nerve. 31 pairs of spinal nerves exist in the body, with each one connecting to the spine via its nerve root. Mapping has been performed and published, which allows one to determine the spinal nerve or nerves that communicate with a specific region of the body. One example would be cervical spinal nerves C5 and C6, which pass signals between the deltoid muscle of the shoulder and the brain.

Treatment of spasticity generally includes physical therapy or occupational therapy targeted at reducing muscle tone, improving range of motion, mobility, comfort, and strength of moveable parts of the body. Botulinum toxin (BTX) is often used to interrupt neuronal signaling by destroying nerve tissue. A variety of medications have been used to treat the symptoms of spasticity. For example, dantrolene reduces the release of calcium into the sarcoplasmic reticulum of muscles, which slows muscle fibers. Baclofen binds to $GABA_B$ receptors in the spinal cord, decreasing stretch reflexes. Medications often include serious side effects, including dizziness, weakness, malaise, fatigue, and diarrhea. Confusion and cognition problems are also common with certain medications. For some patients, the only treatment available is surgical denervation of muscles and tendons. It is apparent that a non-invasive, drug-free method for providing treatment of spasticity is desirable.

SUMMARY

Described herein are methods and systems for novel, effective, treatment for spasticity. Methods and devices described herein can be used without medication. Methods and devices described herein desensitize one or more spinal nerves that connect with a treatment area in the body, thereby providing muscle relaxation.

Repetitive magnetic stimulation (rMS) uses a magnetic field generator that is placed near a target region and generates a series of magnetic field pulses roughly the strength of an MRI scan. One common use of rMS is transcranial stimulation to reduce the symptoms of depression, referred to as repetitive transcranial magnetic stimulation (rTMS).

In one aspect, the subject invention provides methods of treating spasticity in a subject, comprising: (a) determining a treatment location in the body of the subject that is or has been a source of spasticity for the subject; (b) determining a target location on or near at least one spinal nerve that connects the treatment location to the spine ipsilateral to the treatment location; and (c) administering repetitive magnetic field pulses to the target location.

Preferably the magnetic pulses are generated using an electromagnet, but other methods may also be used. The frequency (or frequencies) of magnetic pulses is chosen such that communication in the spinal nerve in the target location is enhanced.

In some embodiments of at least one aspect described above, the magnetic pulse frequency is fixed at or near a target frequency. In some embodiments of at least one aspect described above, the magnetic pulse frequency hops periodically about an average target frequency. In some embodiments of at least one aspect described above, the magnetic pulse frequency hops periodically to random values within a range about an average target frequency. In some embodiments of at least one aspect described above, the magnetic pulse frequency hops periodically in a specific pattern about an average target frequency. In some embodiments of at least one aspect described above, the magnetic pulse frequency hops periodically between two values about an average target frequency. In some embodiments of at least one aspect described above, the magnetic pulse target frequency is from about 1 Hz to about 10 Hz. In some embodiments of at least one aspect described above, the magnetic pulse target frequency is from about 10 Hz to about 30 Hz.

Pulses may be part of a pulse train, with a specific overall duty cycle wherein the pulse train is active for a certain period of time, then inactive, and restarts every duty cycle period for the treatment duration. In some embodiments of at least one aspect described above, the repetitive magnetic pulses are part of a pulse train with a train duration that is about 4 seconds to about 30 seconds and is alternately active and inactive as part of a duty cycle with a period of about 30 seconds to about 80 seconds. In some embodiments of at least one aspect described above, the pulse train duration is about 30 seconds to about 200 seconds and the duty cycle period is about 40 seconds to about 300 seconds.

Treatment may be administered for a length of time necessary to achieve efficacy for the therapy. In some embodiments of at least one aspect described above, the treatment is administered for a treatment duration that is about 0 minutes to about 10 minutes. In some embodiments of at least one aspect described above, the treatment is administered for a treatment duration that is about 10 minutes to about 30 minutes.

The target location is chosen to be at least one portion of the spinal nerve close to the nerve root ipsilateral to the treatment location. In some embodiments of at least one aspect described above, the target location is from about ½ inch to about 2 inches from the spine. In some embodiments of at least one aspect described above, the target location is from about 2 inches to about 4 inches from the spine.

The magnetic field pulse strength should be set to a value that provides effective therapy. In some embodiments of at least one aspect described above, the strength of the magnetic field pulses is from about 10 Gauss to about 4 Tesla. In some embodiments of at least one aspect described above, the strength of the magnetic field pulses is adjusted based on the tolerance of the subject. The tolerance of the subject is based on the threshold above which the magnetic pulses cause unacceptable discomfort in the target location. In some embodiments of at least one aspect described above, the method described herein may be used to treat spasticity caused by at least one of multiple sclerosis, stroke, traumatic brain injury, cerebral palsy, and spinal cord injury, strenuous exercise, muscle recovery, a sports injury, a traumatic injury, post-operative side effect, sympathetic nervous system response to an event, or a neuromuscular injury.

In addition to transmitting magnetic pulses to a target location in the spinal nerve of the subject, improved spasticity reduction may be achieved by administering transcranial magnetic field pulses at a frequency of a biological metric, or a harmonic or sub-harmonic of the biological metric. This stimulation allows for enhanced communication in the pyramidal fibers, allowing improved transmission of inhibitory signals to the motor neurons. In addition, enhanced communication allows sensory neurons to provide improved feedback from the muscle, allowing better control and coordination of the muscle. In some embodiments of at least one aspect described above, the method further comprises administering repetitive transcranial magnetic field pulses at a frequency of a biological metric, or a harmonic or sub-harmonic of the biological metric. In some embodiments of at least one aspect described above, repetitive magnetic pulses are administered transcranially and to the target location concurrently. In some embodiments of at least one aspect described above, repetitive magnetic pulses are administered transcranially and to the target location non-concurrently.

In another aspect of the present invention, a device to treat spasticity in a subject is provided comprising: (a) a magnetic field generator; (b) a power source configured to energize the magnetic field generator in order to generate a repetitive pulsed magnetic field outside a subject (or a connector for connecting to a power source); and (c) an adjustable mount that is configured to hold the magnetic field generator in place; wherein the electrical magnetic field generator is configured to transmit repetitive magnetic field pulses such that the magnetic field induces an electric current or voltage potential in a target location on or near the spinal nerve that connects a spasticity treatment location to the spine.

In some embodiments of at least one aspect described above, the adjustable mount is configured to position the magnetic field generator above the target location, outside but close to the skin of the subject. In some embodiments of at least one aspect described above, the target location is at a distance of about ½ inch to about 4 inches from the spine. In some embodiments of at least one aspect described above, the mount is attached to the body so that the magnetic field generator may be worn by the subject. In some embodiments of at least one aspect described above, the mount is held stationary so that the subject positions his/her body near the mount in order to bring the target location close to the magnetic field generator.

It is possible to incorporate the mount as part of a treatment chair, which allows the person to sit in the chair and adjust his/her body so as to place the magnetic field generator near the target area. Incorporating the mount into a chair makes positioning easier, since the person's body may naturally rest in the correct position. In some embodiments of at least one aspect described above, the mount is part of a treatment chair. The mount does not need to be in a fixed location on the chair. The target location may change based on the treatment location. In addition, the size of people varies so that the treatment location may naturally rest against a different part of the treatment chair. Therefore, it may be advantageous to allow the mount position to be adjustable. In some embodiments of at least one aspect described above, the mount position is adjustable to allow a person to move the magnetic field generator near the target location.

Instead of repositioning the magnetic field generator depending on target location and the size of the person, it may be advantageous to include multiple magnetic field generators in the treatment chair, whereby a particular magnetic field generator or magnetic field generators may be selected to transmit magnetic field pulses, depending on which magnetic field generator is closest to the target location of the person.

The chair embodiment described herein is most relevant for use with a person, other embodiments appropriate for delivering treatment to subjects other than people can be readily envisioned by the skilled artisan having the benefit of the disclosure provided herein.

In some embodiments of at least one aspect described above, the device further comprises a second magnetic field generator as part of the treatment chair, whereby at least one of the magnetic field generators may be selected using a switch to transmit repetitive magnetic stimulation to one or more target locations. In some embodiments of at least one aspect described above, the first magnetic field generator and the second magnetic field generator transmit repetitive magnetic stimulation to target locations concurrently. In some embodiments of at least one aspect described above, the first magnetic field generator and the second magnetic field generator transmit repetitive magnetic stimulation to target locations non-concurrently.

In addition to transmitting magnetic pulses to a target location in the spinal nerve of the subject, improved spasticity reduction may be achieved by administering transcranial magnetic field pulses at a frequency of a biological metric, or a harmonic or sub-harmonic of the biological metric. This stimulation allows for treatment of anxiety associated with the spasticity. By reducing the subject's anxiety, additional relaxation of the muscle is allowed. In some embodiments of at least one aspect described above, the device further comprises a second magnetic field generator and mount in order to transmit repetitive transcranial magnetic field pulses at a frequency of a biological metric, or a harmonic or sub-harmonic of the biological metric. In some embodiments of at least one aspect described above, the first and second magnetic field generators transmit repetitive magnetic stimulation transcranially and to the target location concurrently. In some embodiments of at least one aspect described above, the first and second magnetic field generators transmit repetitive magnetic stimulation transcranially and to the target location non-concurrently.

BRIEF DESCRIPTION OF THE DRAWINGS

A better understanding of the features and advantages of the systems and methods provided will be obtained by reference to the following detailed description that sets forth illustrative embodiments and the accompanying drawings of which.

DETAILED DESCRIPTION

Figure 1:
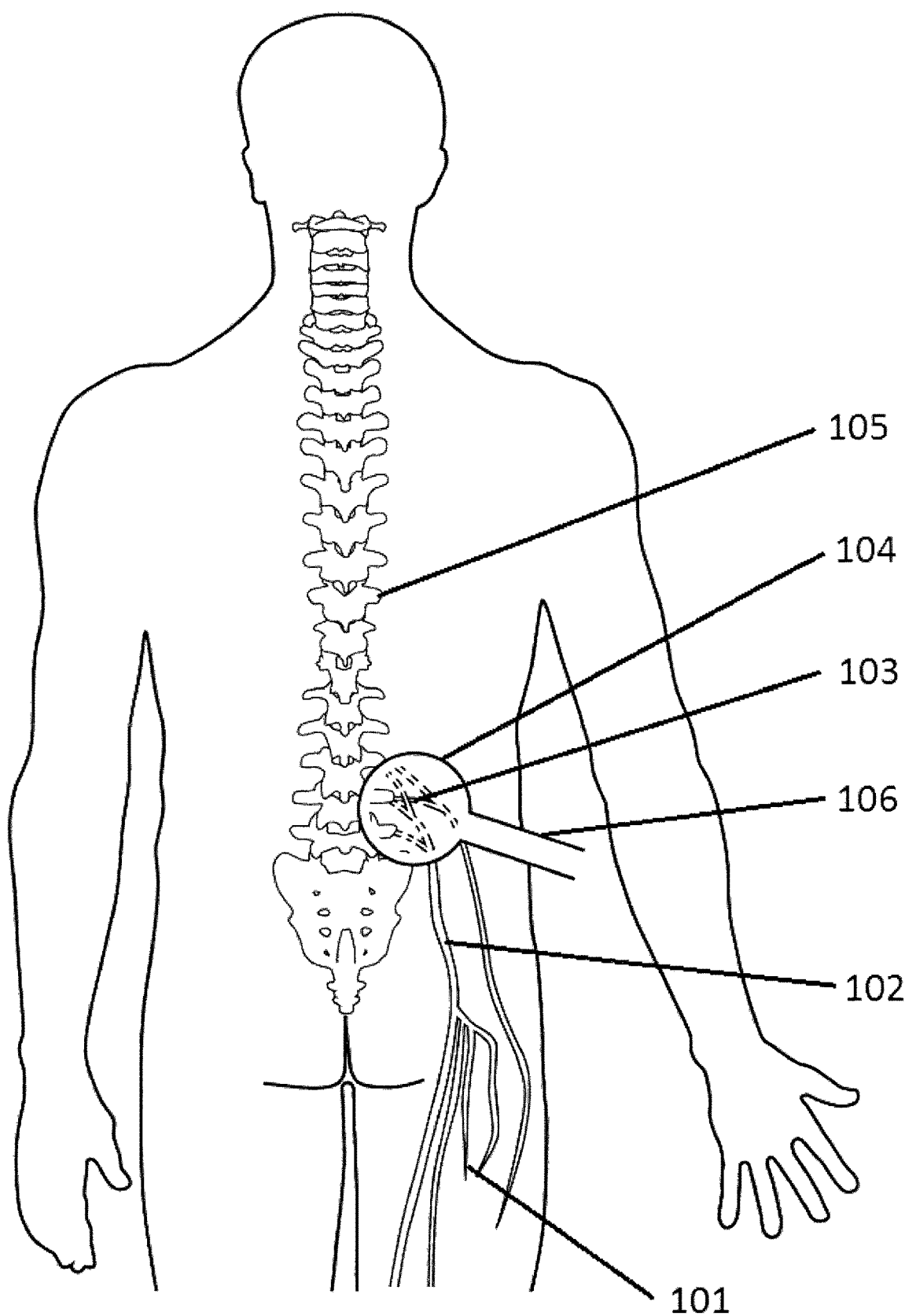
FIG. 1 shows an exemplary device in which the magnetic field generator is a coil that is placed near the root of the spinal nerve connecting the spine to a treatment location in a muscle in the thigh of a subject.

While certain embodiments have been provided and described herein, it will be readily apparent to those skilled in the art that such embodiments are provided by way of example only. It should be understood that various alternatives to the embodiments described herein may be employed, and are part of the invention described herein.

Described herein are methods and systems for novel, effective, treatment of spasticity. In some embodiments, described are methods and systems that transmit repetitive Magnetic Stimulation (rMS) to a target location that includes a portion of at least one spinal nerve, and is located near the root of the spinal nerve where it connects to the spine. The spinal nerve connects the spine with at least one treatment location in the body of the subject. When repetitive magnetic pulses are administered to a target location at a low pulse frequency (less than about 20 Hz), the spinal nerve lying inside or near the target location becomes enhanced, which allows for improvement of the spinal nerve function, thereby allowing the inhibitory nerve pulses to reach the treatment location, causing the muscle to relax, and making movement easier for the subject. In addition, the improved communication in the spinal nerve allows better feedback from the treatment area, allowing improved coordination and control of the muscle. When stimulation is combined with rTMS directed at the cortex with a pulse frequency equal to a harmonic of a biological metric, such as heart rate, that falls in an EEG band of the subject, such as the alpha band, the two treatments together allow for a significant relaxation and control of the person's muscle, thereby reducing the symptoms of spasticity.

The term "treatment location", when referring to the rMS treatment, is a location that is a region of the body that is a source of spasticity for the subject.

The term "target location", when referring to the rMS treatment, is a location near the root of a spinal nerve that connects to the treatment location. The target location is the region of the body where the rMS magnetic pulses are directed.

The term "target frequency", when referring to the rMS treatment, is the frequency of the magnetic pulses. When magnetic pulses are transmitted at a fixed frequency, the target frequency refers to this fixed value. When magnetic pulses are transmitted at a frequency that varies over time, either randomly or with a fixed pattern, the target frequency refers to the average of the magnetic pulse frequencies.

The term "pulse train", when referring to the rMS treatment, is a series of magnetic pulses.

The term "duty cycle", when referring to the rMS treatment, is a periodic time interval when the pulse train is active during a portion of the time interval, where magnetic pulses are generated, and inactive during the remaining portion of the time interval, where magnetic pulses are not generated.

The term "treatment duration", when referring to the rMS treatment, is the total session time. The treatment duration is composed of a series of duty cycles.

The term "magnetic field generator," when referring to the rMS device, is the portion of the device that generates a pulsed magnetic field. Examples of a magnetic field generator include a coil, a moving permanent magnet, or combination thereof. Example coils include a circular coil, a figure-8 coil, and an H-coil. Example movement of a permanent magnet include rotational motion, linear motion, and swing motion. Preferably, the magnetic field generator is an electromagnet, but other methods may also be used to generate a magnetic field.

The term "subject" refers to an animal that can be afflicted with spasticity. The animal is preferably a vertebrate. The animal may be a mammal, including humans, dogs, cats, and horses.

Described herein are methods and devices that provide treatment and involve no medication, although medication may be administered in conjunction with the treatment without necessarily altering the effects of the treatment.

Motor neurons are the primary mechanism for muscle contraction. Upper motor neurons are cortico-spinal interneurons that arise from the motor cortex and descend to the spinal cord. Lower motor neurons proceed from the spinal cord through the spinal nerve and innervate the muscle. Motor neurons, upon adequate stimulation, release neurotransmitters that trigger a response in a muscle fiber, which leads to muscle contraction. The response of a muscle fiber to a neurotransmitter can only be excitatory, or contractile. Muscle relaxation and inhibition of muscle contraction are achieved by inhibition of the motor neuron itself.

Spasticity may be caused by a lesion along the upper motor neuron pathway, which causes the removal of inhibitory influences exerted by the cortex on the postural centers of the vestibular nuclei and reticular formation. This can result following damage to the corticospinal tract.

When a signal is transmitted through the spinal nerve, a minimum transit time is generally required, which is about 50 milliseconds. This means that the highest frequency at which the nerve can fire is about 20 Hz (20 times per second). Magnetic pulses administered to a target location on the spinal nerve cause a voltage potential in the nerve fibers, and if the magnetic pulses have a low frequency (less than 20 Hz), then communication in the spinal nerve becomes enhanced Enhanced efferent communication improves the transmission of inhibitory signals to the motor neurons, which allows for a relaxation of the muscle fiber. In addition, enhanced afferent communication improves the transmission via sensory neurons from the muscle to the spinal cord, allowing better feedback, which improves muscle control and coordination.

The target location may be anywhere along the spinal nerve. However, if magnetic pulses are delivered too close to the spine, other nerves may be affected, causing side effects. The spinal nerve is generally too deep along the mid region for magnetic pulses to have the desired effect. Magnetic pulses generated near the spinal nerve at the treatment location is another potential location where magnetic pulses could have the desired effect.

In one aspect, the subject invention provides methods of treating spasticity in a subject, comprising: (a) determining a treatment location in the body of the subject that is or has been a source of spasticity for the person; and (b) determining a target location on or near at least one spinal nerve that connects the treatment location to the spine ipsilateral to the treatment location; and (c) administering repetitive magnetic field pulses to the target location.

The frequency or frequencies of magnetic pulses is chosen such that communication in the spinal nerve in the target location is enhanced. In some embodiments of at least one aspect described above, the magnetic pulse frequency is fixed at or near a target frequency. In some embodiments of at least one aspect described above, the magnetic pulse frequency hops periodically about an average target frequency. In some embodiments of at least one aspect described above, the magnetic pulse frequency hops periodically to random values within a range about an average target frequency. In some embodiments of at least one aspect described above, the magnetic pulse frequency hops periodically in a specific pattern about an average target frequency. In some embodiments of at least one aspect described above, the magnetic pulse frequency hops periodically between two values about an average target frequency. In some embodiments of at least one aspect described above, the magnetic pulse target frequency is from about 1 Hz to about 10 Hz. In some embodiments of at least one aspect described above, the magnetic pulse target frequency is from about 10 Hz to about 30 Hz.

Pulses may be part of a pulse train, with a specific overall duty cycle wherein the pulse train is active for a certain period of time, then inactive, and restarts every duty cycle period for the treatment duration. In some embodiments of at least one aspect described above, the repetitive magnetic pulses are part of a pulse train with a train duration that is about 4 seconds to about 30 seconds and is alternately active and inactive as part of a duty cycle with a period of about 30 seconds to about 80 seconds. In some embodiments of at least one aspect described above, the pulse train duration is about 30 seconds to about 200 seconds and the duty cycle period is about 40 seconds to about 300 seconds.

Treatment duration may be administered for a length of time necessary to achieve efficacy for the therapy. In some embodiments of at least one aspect described above, the treatment is administered for a treatment duration that is about 0 minutes to about 10 minutes. In some embodiments of at least one aspect described above, the treatment is administered for a treatment duration that is about 10 minutes to about 30 minutes.

The target location is chosen to be at least one portion of the spinal nerve close to the nerve root ipsilateral to the treatment location. In some embodiments of at least one aspect described above, the target location is from about ½ inch to about 2 inches from the spine. In some embodiments of at least one aspect described above, the target location is from about 2 inches to about 4 inches from the spine.

The magnetic field pulse strength may be set to the value that provides effective therapy. In some embodiments of at least one aspect described above, the strength of the magnetic field pulses is from about 10 Gauss to about 4 Tesla. In some embodiments of at least one aspect described above, the strength of the magnetic field pulses is adjusted based on the tolerance of the subject. The tolerance of the subject is based on the threshold above which the magnetic pulses cause unacceptable discomfort in the target location. In some embodiments of at least one aspect described above, the method described herein may be used to treat spasticity caused by at least one of multiple sclerosis, stroke, traumatic brain injury, cerebral palsy, spinal cord injury, strenuous exercise, muscle recovery, a sports injury, a traumatic injury, post-operative side effect, sympathetic nervous system response to an event, or a neuromuscular injury. One example of a post-operative side effect is constriction of the bowels, causing constipation. One example of a sympathetic nervous system response to an event is constriction of the urethra, causing urine retention.

In addition to transmitting magnetic pulses to a target location in the spinal nerve of the subject, improved spasticity reduction may be achieved by administering transcranial magnetic field pulses at a frequency of a biological metric, or a harmonic or sub-harmonic of the biological metric. This stimulation allows for enhanced communication in the pyramidal fibers, allowing improved transmission of inhibitory signals to the motor neurons. In addition, enhanced communication allows sensory neurons to provide improved feedback from the muscle, allowing better control and coordination of the muscle. In some embodiments of at least one aspect described above, the method further comprises administering repetitive transcranial magnetic field pulses at a frequency of a biological metric, or a harmonic or sub-harmonic of the biological metric. In some embodiments of at least one aspect described above, repetitive magnetic pulses are administered transcranially and to the target location concurrently. In some embodiments of at least one aspect described above, repetitive magnetic pulses are administered transcranially and to the target location non-concurrently.

In another aspect of the present invention, a device to treat spasticity in a subject is provided comprising:
  a. A magnetic field generator;
  b. a power source configured to energize the magnetic field generator in order to generate a repetitive pulsed magnetic field outside a subject, or a connector for connecting to a power source; and
  c. an adjustable mount that is configured to hold the magnetic field generator in place;
wherein the magnetic field generator is configured to transmit repetitive magnetic field pulses such that the magnetic field induces an electric current or voltage potential in a target location on or near the spinal nerve that connects a spasticity treatment location to the spine.

In some embodiments of at least one aspect described above, the adjustable mount is configured to position the magnetic field generator above the target location, outside but close to the skin of the subject. In some embodiments of at least one aspect described above, the target location is at a distance of about ½ inch to about 4 inches from the spine. In some embodiments of at least one aspect described above, the mount is attached to the body so that the magnetic field generator may be worn by the subject. In some embodiments of at least one aspect described above, the mount is held stationary so that the subject positions his/her body near the mount in order to bring the target location close to the magnetic field generator.

It is possible to incorporate the mount as part of a treatment chair, which allows the person to sit in the chair and adjust his/her body so as to place the magnetic field generator near the target area. Incorporating the mount into a chair makes positioning easier, since the person's body may naturally rest in the correct position. In some embodiments of at least one aspect described above, the mount is part of a treatment chair.

The mount does not need to be in a fixed location on the chair. The target location may change based on the treatment location. In addition, the size of people varies so that the treatment location may naturally rest against a different part of the treatment chair. Therefore, it may be advantageous to allow the mount position to be adjustable. In some embodiments of at least one aspect described above, the mount position is adjustable to allow a person to move the magnetic field generator near the target location.

Instead of repositioning the magnetic field generator depending on target location and the size of the person, it may be advantageous to include multiple magnetic field generators in the treatment chair, whereby a particular magnetic field generator or magnetic field generators may be selected to transmit magnetic field pulses, depending on which magnetic field generator is closest to the target location of the person. In some embodiments of at least one aspect described above, the device further comprises a second magnetic field generator as part of the treatment chair, whereby at least one of the magnetic field generators may be selected using a switch to transmit repetitive magnetic stimulation to one or more target locations.

In some embodiments of at least one aspect described above, the first magnetic field generator and the second magnetic field generator transmit repetitive magnetic stimulation to target locations concurrently. In some embodiments of at least one aspect described above, the first magnetic field generator and the second magnetic field generator transmit repetitive magnetic stimulation to target locations non-concurrently.

In addition to transmitting magnetic pulses to a target location in the spinal nerve of the person, improved spasticity reduction may be achieved by administering transcranial magnetic field pulses at a frequency of a biological metric, or a harmonic or sub-harmonic of the biological metric. This stimulation allows for treatment of anxiety associated with the spasticity. By reducing the subject's anxiety, additional relaxation of the muscle is allowed. In some embodiments of at least one aspect described above, the device further comprises a second magnetic field generator and mount in order to transmit repetitive transcranial magnetic field pulses at a frequency of a biological metric, or a harmonic or sub-harmonic of the biological metric. In some embodiments of at least one aspect described above, the first and second magnetic field generators transmit repetitive magnetic stimulation transcranially and to the target location concurrently. In some embodiments of at least one aspect described above, the first and second magnetic field generators transmit repetitive magnetic stimulation transcranially and to the target location non-concurrently.

FIG. 1 shows an exemplary device in which the spinal nerve (102) connects a location on the spine (105) to a treatment location in a muscle (101) in the subject's right leg. The magnetic field generator is a coil (104) in a handheld mount (106) that is placed so that the coil is above a target location (103) that includes a portion of the spinal nerve near the nerve root. Although this figure shows a handheld mount, the mount could also be affixed to a stationary bracket or other mechanism in order to prevent the coil from shifting away from the target location.

Figure 2:
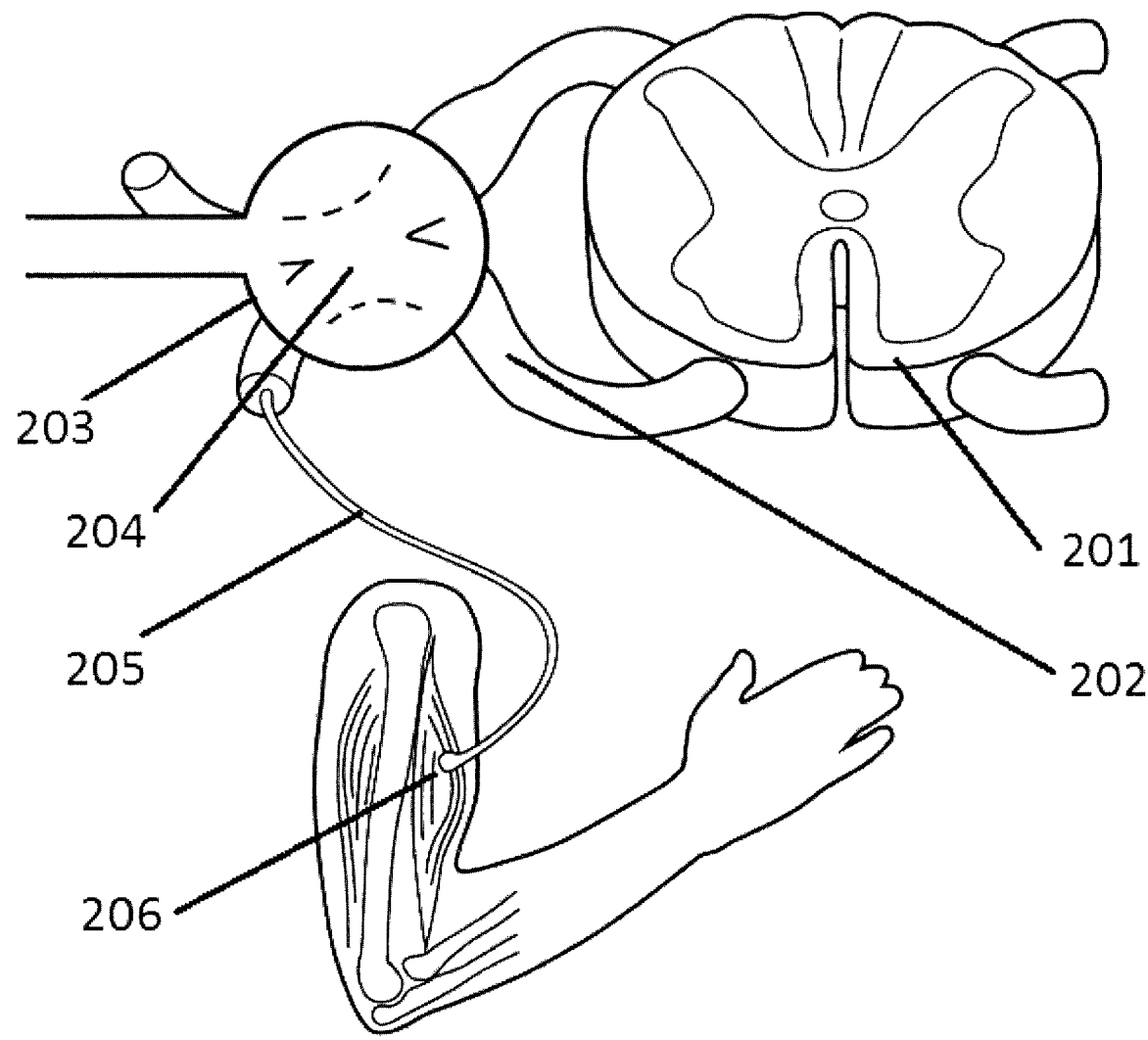
FIG. 2 shows an example target location near the nerve root of a spinal nerve connecting the spine to a treatment location in a muscle of a subject.

FIG. 2 shows an example of a target location in which the spinal nerve (205) connects a location on the spine (201) to a treatment location in a muscle (206). The magnetic field generator is a coil (203) that is placed over the target location (204), which is located near the nerve root (202) of the spinal nerve where a connection is made to the spine.

Figure 3:
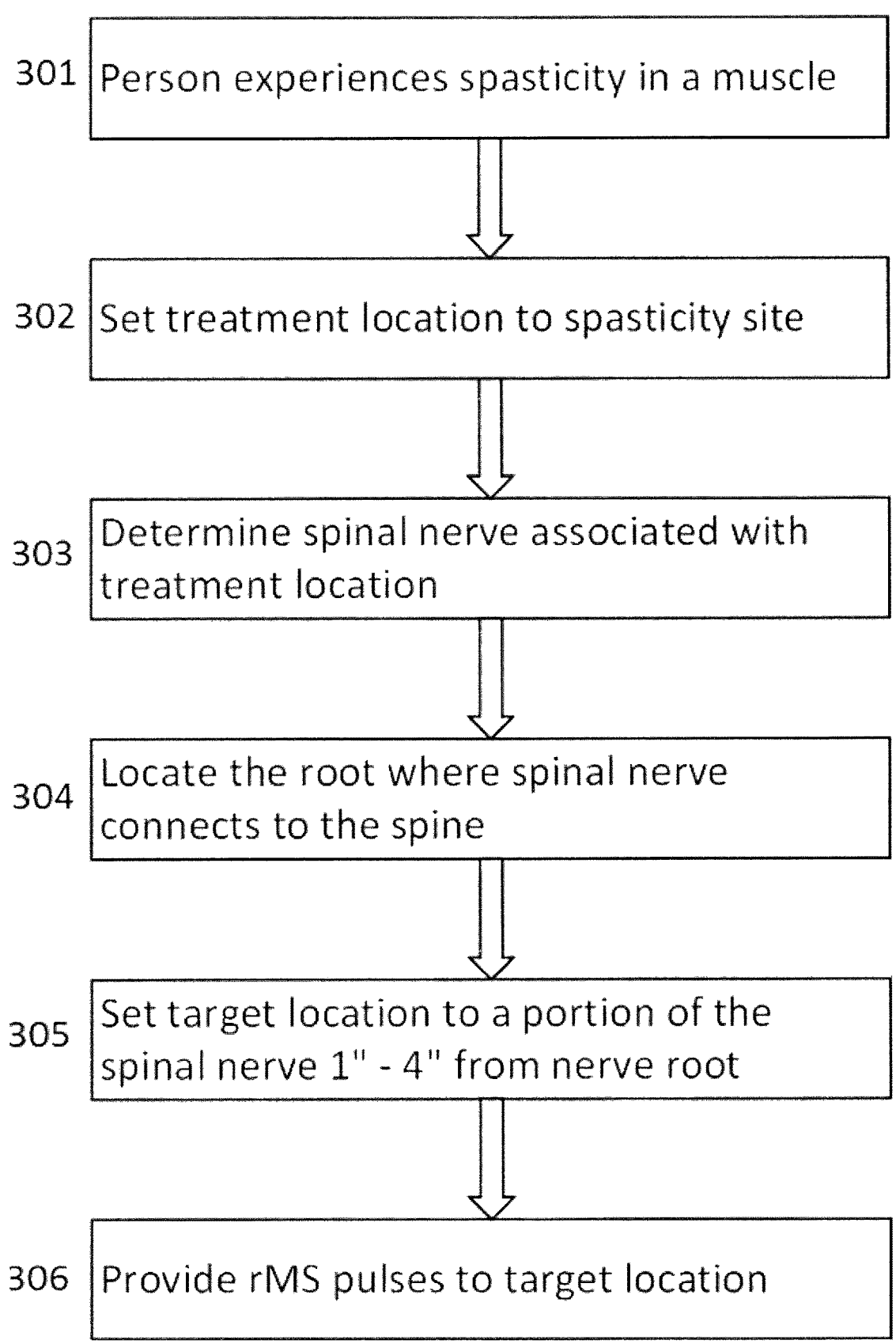
FIG. 3 shows an example method flowchart in which the source of spasticity is localized and treatment is performed at a target location.

FIG. 3 shows an exemplary flowchart for one aspect of the method described herein, where a subject experiences spasticity (301) in a portion of the body. The location where the spasticity occurs is registered as the treatment location (302). One or more spinal nerves connect the treatment location to the spine. These may be determined anatomically using existing references (303). Once a spinal nerve is identified as connecting the spine to the treatment location, the root of the spinal nerve is found adjacent to the spine ipsilateral to the treatment location (304). The target location is registered to a portion of the spinal nerve about 1 inch to 4 inches from the nerve root (305). Repetitive magnetic pulses (rMS) are administered to the target location (306) in order to enhance communication in the spinal nerve and relax the muscle.

Figure 4:
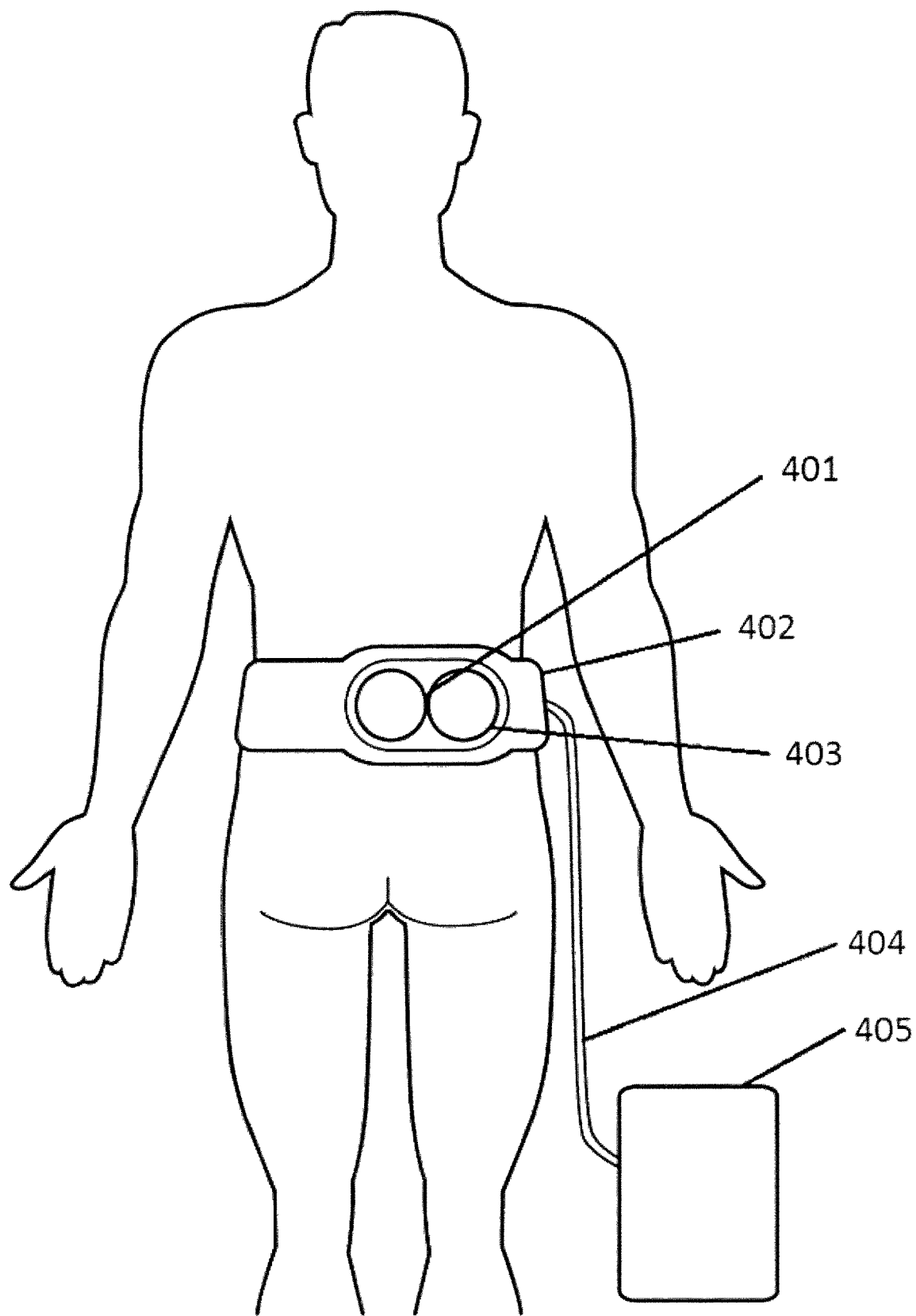
FIG. 4 shows an exemplary device in which the magnetic field generator is a coil that is held near the target location using a strap that goes around the waist or torso of the person.
Figure 8:
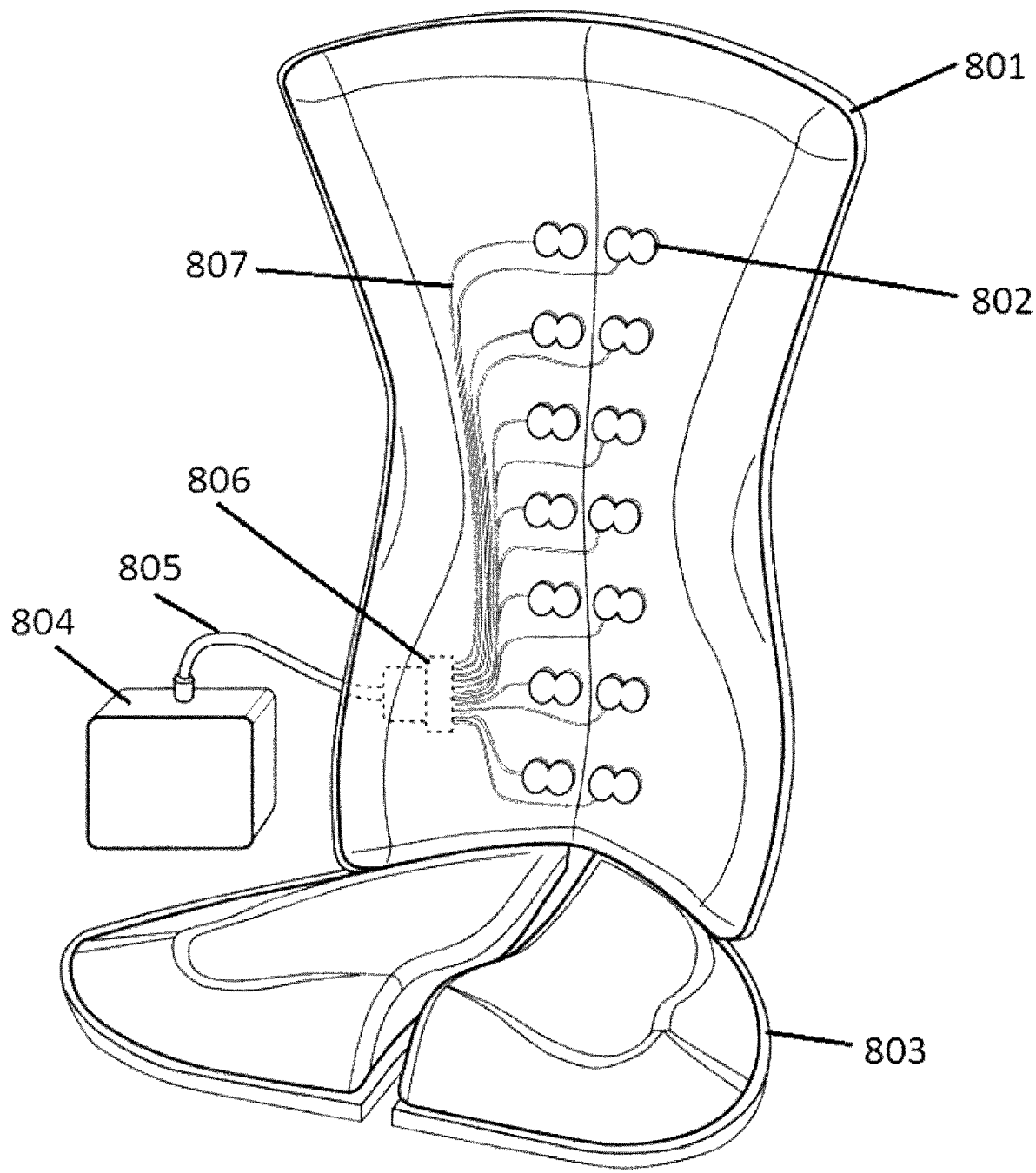
FIG. 8 shows an exemplary device in which a series of figure-8 coils are incorporated into the back of a treatment chair. Through the use of a switch, at least one of the coils may be selected to target one or more spinal nerves.

FIG. 4 shows an exemplary device in which the magnetic field generator is a figure-8 magnetic coil (403) that is contained inside a strap (402), which encircles the torso of the subject. This strap is configured so that the magnetic pulses generated by the coil are directed to the target location (401). A cable (404) connects the coil with a power module (405), which controls the generation of the current pulses required to create the magnetic field pulses in the coil. The strap is shown on the subject's lower waist. However, in some embodiments the strap can be raised or lowered in order to cover other target areas. Also, the coil location on the strap may be shifted so that the coil rests either a greater or lesser distance from the spine, or on the opposite side of the spine.

Figure 5:
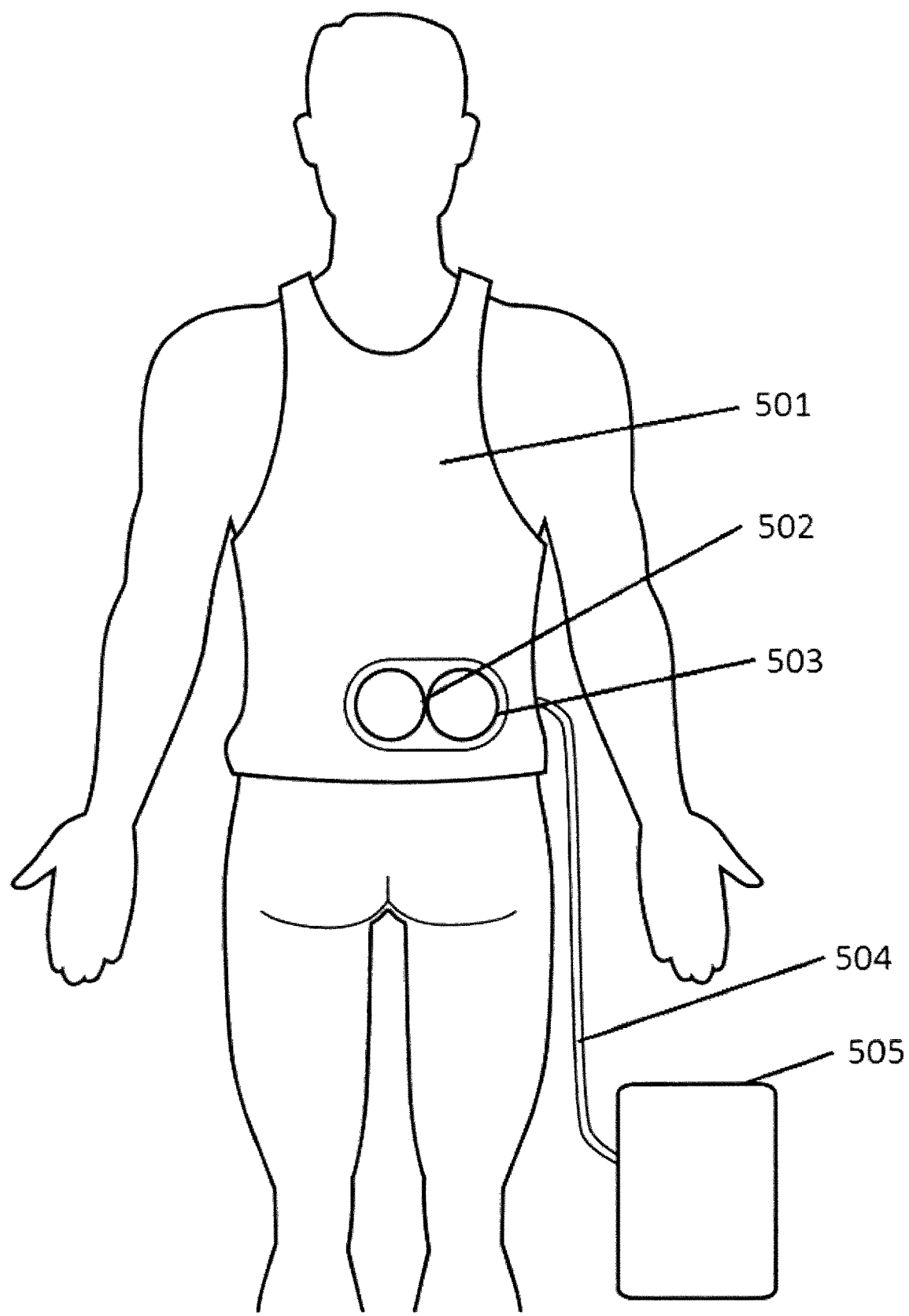
FIG. 5 shows an exemplary device in which the magnetic field generator is a coil that is contained in a vest in a location that is near the target location.

FIG. 5 shows an exemplary device in which the magnetic field generator is a figure-8 magnetic coil (503) that is contained as part of a vest (501), which is worn by the subject. The vest is configured so that the magnetic pulses generated by the coil are directed to the target location (502). A cable (504) connects the coil with a power module (505), which controls the generation of the current pulses required to create the magnetic field pulses. This shows the coil over a target location situated on the subject's waist. However, in some embodiments the position of the coil could be changed, either using a vest with a pocket in a different location, or by allowing the user or caregiver to adjust the coil position using Velcro or some other mechanism to secure the device in place.

Figure 6:
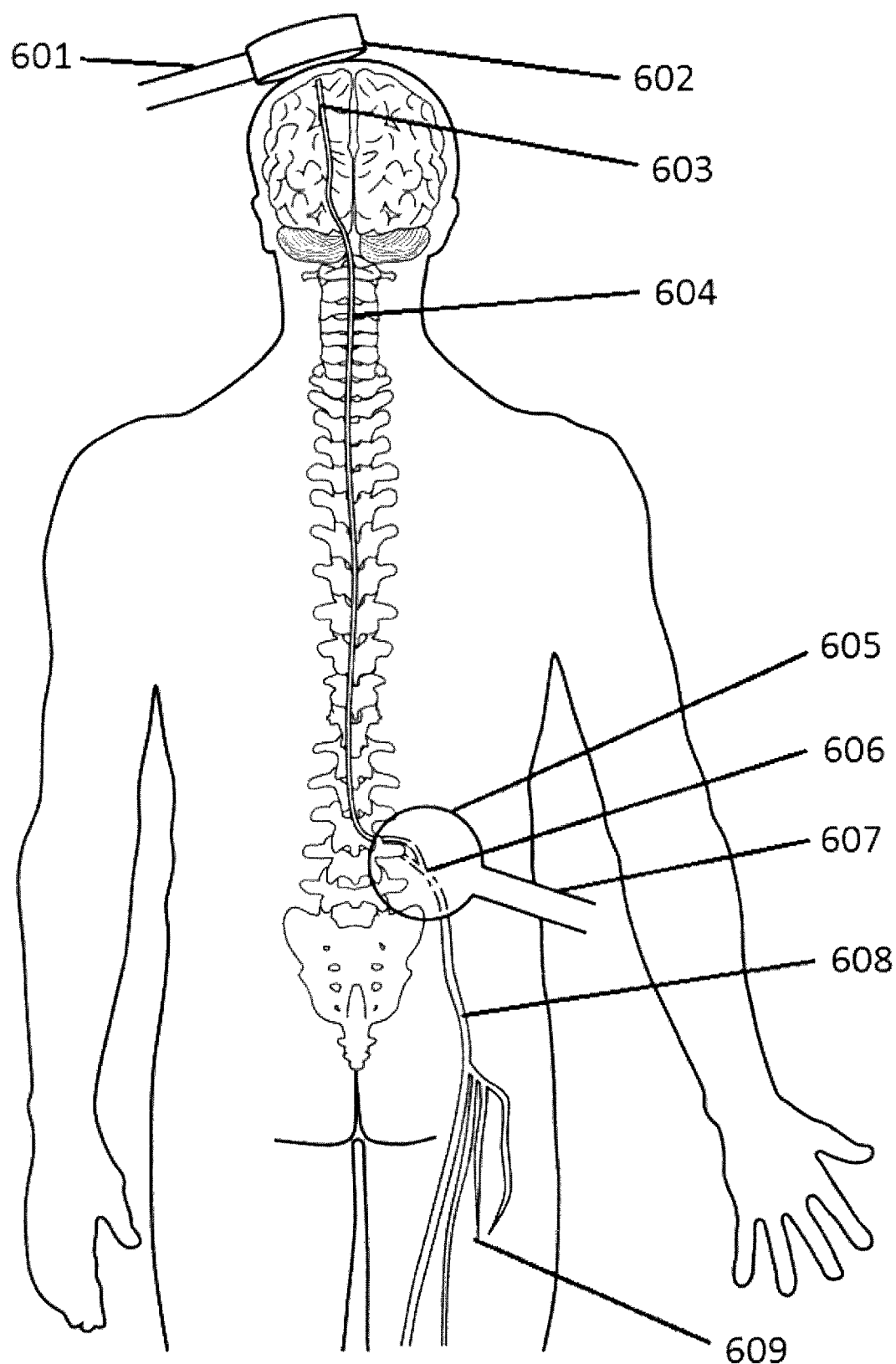
FIG. 6 shows an exemplary device in which an rTMS coil is placed near the head and a second coil is placed near a target location.

FIG. 6 shows an exemplary device in which the spinal nerve (608) connects a location on the spine to a treatment location in a muscle (609) in the subject's right leg. A coil (605) in a handheld mount (607) is placed so that the coil is above a target location (606) that includes a portion of the spinal nerve near the nerve root. Also shown is a second coil (602) in a handheld mount (601) that delivers transcranial magnetic stimulation to the brain of the subject. This stimulation enhances communication in the pyramidal neuron (603) that connects to the spinal cord (604).

Figure 7:
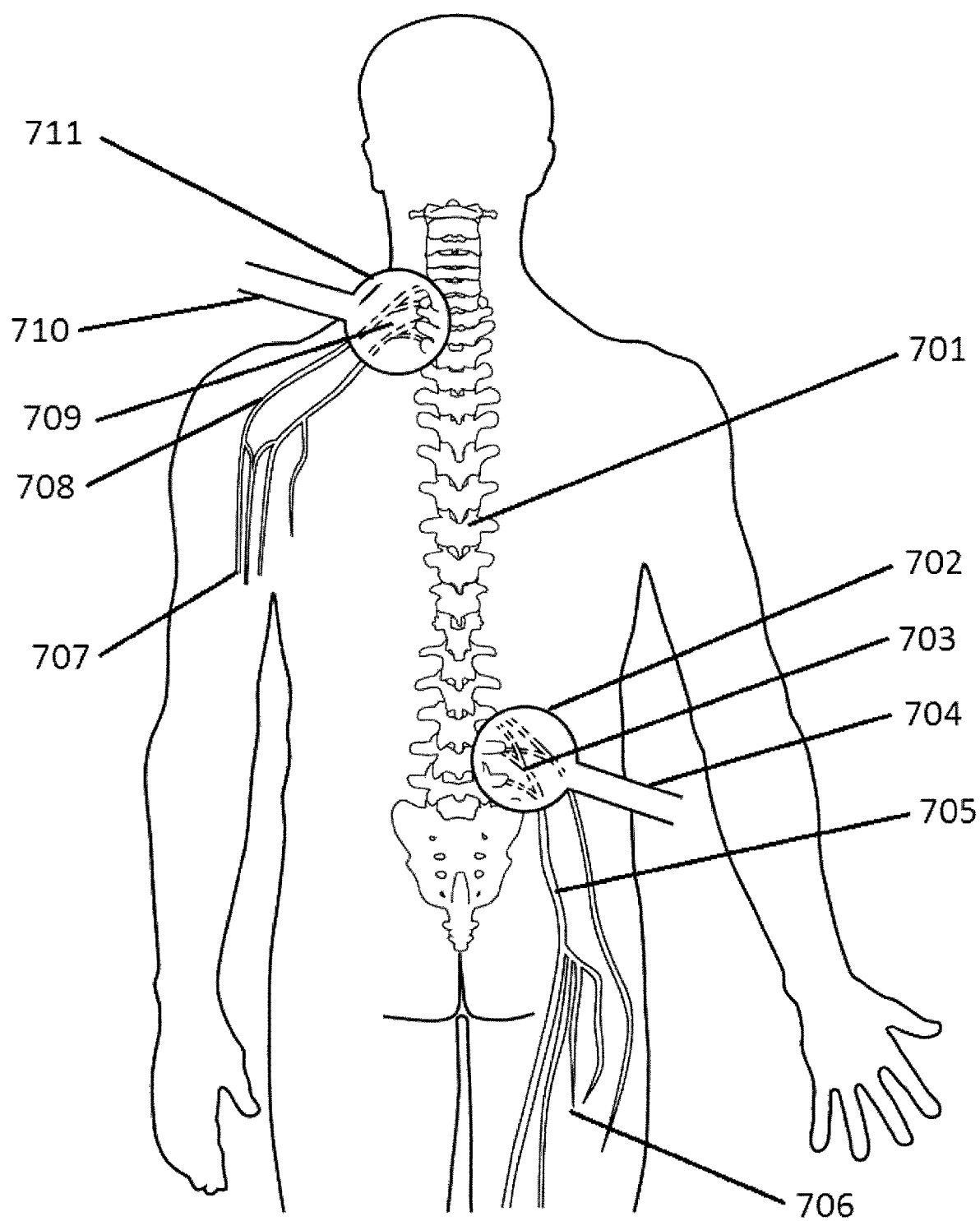
FIG. 7 shows an exemplary device in which two coils are placed near the roots of two separate spinal nerves, allowing magnetic pulses to be applied to two separate target locations in order to affect two separate treatment locations.

FIG. 7 shows an exemplary device in which 2 coils are used to administer magnetic pulses to 2 different treatment areas during the same treatment session. A treatment area in the thigh (706) is connected to the spine (701) through a spinal nerve (705). The coil (702) in a mount (704) is positioned so that magnetic field pulses are delivered to the target area (703). A second treatment area in the arm (707) is connected to a different area of the spine through a spinal nerve (708). The second coil in a mount (710) is positioned so that magnetic field pulses are delivered to the second target area (709). This figure shows two coils. However, in some embodiments more than two coils could be used to stimulate more than two target areas.

Since 31 pairs of spinal nerves exist in a person, and because magnetic pulses affect a fairly wide area, when a magnetic field generator is positioned to transmit magnetic field pulses to one target area of one spinal nerve, other spinal nerves could also be affected. In some embodiments, a single spinal nerve is affected. In some embodiments, two spinal nerves are affected. In some embodiments, three spinal nerves are affected. In some embodiments, more than three spinal nerves are affected. Affecting multiple spinal nerves with a single magnetic field generator allows the option of treatment of multiple target areas with a single magnetic field generator.

FIG. 8 shows an exemplary device in which fourteen figure-8 coils (802) are incorporated into the back of a treatment chair (801). The coils are arranged on either side of the midline of the chair. The coils are connected via cables (807) to a switch (806) that connects to the power module (804) by a cable (805). This configuration allows selective activation of one or more coils to treat one or more target areas on either side of the spine.

Unless the context clearly requires otherwise, throughout the description and the claims, the words "comprise," "comprising," and the like are to be construed in an inclusive sense as opposed to an exclusive or exhaustive sense; that is to say, in a sense of "including, but not limited to." Words using the singular or plural number also include the plural or singular number respectively. Additionally, the words "herein," "hereunder," "above," "below," and words of similar import refer to this application as a whole and not to any particular portions of this application. When the word "or" is used in reference to a list of two or more items, that word covers all of the following interpretations of the word: any of the items in the list, all of the items in the list and any combination of the items in the list.

The above descriptions of illustrated embodiments of the system, methods, or devices are not intended to be exhaustive or to be limited to the precise form disclosed. While specific embodiments of, and examples for, the system, methods, or devices are described herein for illustrative purposes, various equivalent modifications are possible within the scope of the system, methods, or devices, as those skilled in the relevant art will recognize. The teachings of the system, methods, or devices provided herein can be applied to other processing systems, methods, or devices, not only for the systems, methods, or devices described.

The elements and acts of the various embodiments described can be combined to provide further embodiments. These and other changes can be made to the system in light of the above detailed description.

In general, in the following claims, the terms used should not be construed to limit the system, methods, or devices to the specific embodiments disclosed in the specification and the claims, but should be construed to include all processing systems that operate under the claims. Accordingly, the system, methods, and devices are not limited by the disclosure, but instead the scopes of the system, methods, or devices are to be determined entirely by the claims.

While certain aspects of the system, methods, or devices are presented below in certain claim forms, the inventor contemplates the various aspects of the system, methods, or devices in any number of claim forms. Accordingly, the inventors reserve the right to add additional claims after filing the application to pursue such additional claim forms for other aspects of the system, methods, or devices.

EMBODIMENTS

Specific embodiments of the invention include the following:
1. A method of treating spasticity in a subject comprising:
    a. determining a treatment location in the body of the subject that is or has been a source of spasticity for the subject;
    b. determining a target location on or near at least one spinal nerve that connects the treatment location to the spine ipsilateral to the treatment location; and
    c. administering repetitive magnetic field pulses to the target location.
2. The method of Embodiment 1 wherein the magnetic pulse frequency is fixed at or near a target frequency.
3. The method of Embodiment 1 wherein the magnetic pulse frequency hops periodically about an average target frequency.
4. The method of Embodiment 3 wherein the magnetic pulse frequency hops periodically to random values within a range about an average target frequency.
5. The method of Embodiment 3 wherein the magnetic pulse frequency hops periodically in a specific pattern about an average target frequency.
6. The method of Embodiment 3 wherein the magnetic pulse frequency hops periodically between two values about an average target frequency.
7. The method of Embodiment 2 or 3 wherein the magnetic pulse target frequency is from about 1 Hz to about 10 Hz.
8. The method of Embodiment 2 or 3 wherein the magnetic pulse target frequency is from about 10 Hz to about 30 Hz.
9. The method of Embodiment 2 or 3 wherein the repetitive magnetic pulses are part of a pulse train with a train duration that is about 4 seconds to about 30 seconds and is alternately active and inactive as part of a duty cycle with a period of about 30 seconds to about 80 seconds.
10. The method of Embodiment 2 or 3 wherein the repetitive magnetic pulses are part of a pulse train with a train duration that is about 30 seconds to about 200 seconds and is alternately active and inactive as part of a duty cycle with a period of about 40 seconds to about 300 seconds.
11. The method of Embodiment 1 wherein treatment is administered for a treatment duration that is about 0 minutes to about 10 minutes.
12. The method of Embodiment 1 wherein treatment is administered for a treatment duration that is about 10 minutes to about 30 minutes.
13. The method of Embodiment 1 wherein the target location is from about ½ inch to about 2 inches from the spine.
14. The method of Embodiment 1 wherein the target location is from about 2 inches to about 4 inches from the spine.
15. The method of Embodiment 1 wherein the strength of the magnetic field pulses is from about 10 Gauss to about 4 Tesla.
16. The method of Embodiment 15 wherein the strength of the magnetic field pulses is adjusted based on the tolerance of the subject.

17. The method of Embodiment 1 wherein the spasticity is caused by at least one of multiple sclerosis, stroke, traumatic brain injury, cerebral palsy, spinal cord injury, strenuous exercise, muscle recovery, a sports injury, a traumatic injury, post-operative side effect, sympathetic nervous system response to an event, or a neuromuscular injury.

18. The method of Embodiment 1, further comprising administering repetitive transcranial magnetic field pulses at a frequency of a biological metric, or a harmonic or sub-harmonic of the biological metric.

19. The method of Embodiment 18 wherein repetitive magnetic pulses are administered transcranially and to the target location concurrently.

20. The method of Embodiment 18 wherein repetitive magnetic pulses are administered transcranially and to the target location non-concurrently.

21. A device to treat spasticity in a person comprising:
   a. an magnetic field generator; and
   b. a power source configured to energize the magnetic field generator in order to generate a repetitive pulsed magnetic field outside a subject, or a connector for connecting to a power source; and
   c. a mount that is configured to hold the magnetic field generator in place;
   wherein the magnetic field generator is configured to transmit repetitive magnetic field pulses such that the magnetic field induces an electric current or voltage potential in a target location on or near the spinal nerve that connects a spasticity treatment location to the spine.

22. The device of Embodiment 21, wherein the target location is at a distance of about ½ inch to about 4 inches from the spine.

23. The device of Embodiment 21, wherein the mount is attached to the body so that the magnetic field generator may be worn by the subject.

24. The device of Embodiment 21, wherein the mount is held stationary so that the subject positions his/her body near the mount in order to bring the target location close to the magnetic field generator.

25. The device of Embodiment 24 wherein the mount is part of a treatment chair.

26. The device of Embodiment 25 wherein the mount position is adjustable to allow a person to move the magnetic field generator near the target location.

27. The device of Embodiment 25 further comprising a second magnetic field generator as part of the treatment chair, whereby at least one of the magnetic field generators may be selected using a switch to transmit repetitive magnetic stimulation to one or more target locations.

28. The device of Embodiment 27 wherein the first magnetic field generator and the second magnetic field generator transmit repetitive magnetic stimulation to target locations concurrently.

29. The device of Embodiment 27 wherein the first magnetic field generator and the second magnetic field generator transmit repetitive magnetic stimulation to target locations non-concurrently.

30. The device of Embodiment 25 further comprising a second magnetic field generator and mount in order to transmit repetitive transcranial magnetic field pulses at a frequency of a biological metric, or a harmonic or sub-harmonic of the biological metric.

31. The device of Embodiment 30 wherein the first and second magnetic field generators transmit repetitive magnetic stimulation transcranially and to the target location concurrently.

32. The device of Embodiment 30 wherein the first and second magnetic field generators transmit repetitive magnetic stimulation transcranially and to the target location non-concurrently.

33. The device of Embodiment 21 wherein the magnetic field generator is a coil.

While embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

EXAMPLES

The invention is described in greater detail by the following non-limiting examples.

Example 1

A 33-year-old female suffered a right cerebrovascular accident 3 years prior to treatment. She had complete rigidity in her left arm into the digits. She presented with positive Babinski sign and required assistance to walk. The C4 spinal nerve was identified as connecting the spine to the muscles in her arm. Treatment was administered approximately one inch from the spine ipsilateral to the treatment location. Treatment was also administered to the spinal nerve at the left elbow, rMS was administered alternating between treatment locations at 3000 Gauss pulse intensity, 3 Hz pulse frequency, with a pulse train duration of 200 seconds. Following 1 month of stimulation, she had 40% reduction in arm spasticity and recovery of fine motor movement in her hand.

Example 2

A 42-year-old male experienced intracerebral hemorrhage approximately 14 months prior to magnetic stimulation, resulting in right hemiplegia, loss of sensation, and motor weakness in the right upper and lower extremities and tremor in the right appendages. The C5 spinal nerve was identified as connecting the spine to the muscles of the right appendages. The L4 spinal nerve was identified as connecting the spine to the muscles of the right lower extremities.

Treatment was administered approximately one inch from the spine ipsilateral to the treatment location, alternating between the two spinal nerves. Treatment was also administered to the C5 spinal nerve at the right elbow, and to the L4 spinal nerve at the knee and calf. rMS was administered alternately between treatment locations at 8,500 Gauss pulse intensity, 3 Hz pulse frequency, with a pulse train duration of 40 seconds and a duty cycle period of 44 seconds.

Following two weeks of stimulation, tremors in the right appendages decreased significantly, with improved fine motor movement in the digits. Sensation, strength, and control improved significantly in the upper and lower limbs.

Example 3

A 30-year-old male sustained traumatic brain injury due to a bullet through the skull. He experienced left side paralysis, pain in his left shoulder and severe spasticity in his left arm, and absent muscle tone in his left leg. He was Babinski positive, with high muscle tone in the sphincter, and was wheelchair bound. The C4 spinal nerve was identified as connecting the spine to the muscles of the left arm.

Treatment was administered approximately one inch from the spine ipsilateral to the treatment location. In addition, treatment was administered to the spinal nerve near the left elbow. The spinal nerve L3 and Si were identified as connecting the spine to the muscles of the left leg. Treatment was administered approximately one inch from the spine ipsilateral to the treatment location. In addition, treatment was administered to the spinal nerve near the pubococcygeus muscle and left knee. rMS was administered alternately to different locations at 8,000 Gauss pulse intensity, 3 Hz pulse frequency, with a single pulse train duration of 200 seconds per location.

Following six months of stimulation, the person could support his own weight and walk with cane assistance. Reduction in spasticity was noted in the left arm, with similar reduction in spasticity in the sphincter, allowing the person to control urinary flow.

What is claimed is:

1. A device to treat spasticity in a subject comprising:
   a. a first magnetic field generator;
   b. a second magnetic field generator;
   c. a power source configured to energize the first magnetic field generator and generate a repetitive pulsed magnetic field outside the subject;
   d. a first mount that is configured to hold the first magnetic field generator in place; and
   e. a second mount that is configured to hold the second magnetic field generator in place,
   wherein the first magnetic field generator is configured to transmit repetitive magnetic field pulses to induce an electric current or voltage potential in a target location that connects a spasticity treatment location to the spine,
   wherein the first mount is either a wearable vest or a chair back,
   wherein the target location is on a spinal nerve ½ to 4 inches away from a spine of the subject during use of the first mount;
   wherein the second magnetic field generator is configured to transmit repetitive transcranial magnetic field pulses at a frequency of a biological metric, or a harmonic or a sub-harmonic of the biological metric, the repetitive transcranial magnetic field pulses of the second magnetic field generator being delivered while also delivering the repetitive magnetic field pulses of the first magnetic field generator; and
   wherein the spasticity in the subject is treated by the combination of the repetitive magnetic field pulses and the repetitive transcranial magnetic field pulses.

2. The device of claim 1, wherein the first mount is configured to be worn on a body of the subject.

3. The device of claim 1, wherein the first mount is configured to be held stationary.

4. The device of claim 3, wherein the first mount is a chair back, and wherein the first mount is part of a treatment chair.

5. The device of claim 4, wherein a position of the first mount is configured to be adjustable to move the first magnetic field generator near the target location.

6. The device of claim 4, further comprising the second magnetic field generator as part of the treatment chair, whereby at least one of the first magnetic field generator of the treatment chair and the second magnetic field generator of the treatment chair is configured to be selected by a switch to transmit repetitive magnetic stimulation to one or more target locations.

7. The device of claim 6, wherein the first magnetic field generator of the treatment chair and the second magnetic field generator of the treatment chair are configured to transmit repetitive magnetic stimulation to target locations concurrently.

8. The device of claim 6, wherein the first magnetic field generator of the treatment chair and the second magnetic field generator of the treatment chair are configured to transmit repetitive magnetic stimulation to target locations non-concurrently.

9. The device of claim 1, wherein the first magnetic field generator and the second magnetic field generator are configured to transmit repetitive magnetic stimulation respectively to the target location and transcranially concurrently.

10. The device of claim 1, wherein the first magnetic field generator and the second magnetic field generator are configured to transmit repetitive magnetic stimulation respectively to the target location and transcranially non-concurrently.

11. The device of claim 1, wherein the magnetic field generator is a coil.

* * * * *